United States Patent [19]

Fejes et al.

[11] Patent Number: 4,626,242

[45] Date of Patent: Dec. 2, 1986

[54] SIPHON-CARTRIDGE ACTIVATED AUTOMATIC INOCULATING DEVICE WIHTOUT NEEDLE FOR INDIVIDUAL ACCULATION, E.G. FOR INSULINIZATION

[75] Inventors: Kálmán Fejes; Lajos Nagy, both of Budapest, Hungary

[73] Assignee: Radelkis Elektrokémiai Müszergyártó Ipari Szövetkezet, Budapest, Hungary

[21] Appl. No.: 624,584

[22] Filed: Aug. 23, 1984

[51] Int. Cl.⁴ .............................................. A61M 5/30
[52] U.S. Cl. ..................................................... 604/68
[58] Field of Search ........................ 604/68, 70, 71, 72

[56] References Cited

U.S. PATENT DOCUMENTS

| | | | |
|---|---|---|---|
| 3,130,723 | 4/1964 | Venditty et al. | 604/70 |
| 3,526,225 | 9/1970 | Isobe | 604/71 |
| 3,561,443 | 2/1971 | Banker | 604/70 |
| 3,908,651 | 9/1975 | Fudge | 604/71 |
| 4,342,310 | 8/1982 | Lindmayer et al. | 604/71 |
| 4,400,171 | 8/1983 | Dettbarn et al. | 604/68 |
| 4,403,986 | 9/1983 | Dettbarn et al. | 604/70 |

*Primary Examiner*—John D. Yasko

[57] ABSTRACT

In an inoculating apparatus between the inoculating unit and the actuating unit a quick coupling mechanism is inserted. The inoculating device itself becomes actuated by means of a siphon-cartridge via a valve performing a triple function.

The structure ensures the discharge of the carbonic acid gas quantity required for operation through the bore of the piston, simultaneously it prevents further outflow of the carbonic acid gas from the cartridge after work performance.

2 Claims, 1 Drawing Figure

U.S. Patent
Dec. 2, 1986
4,626,242
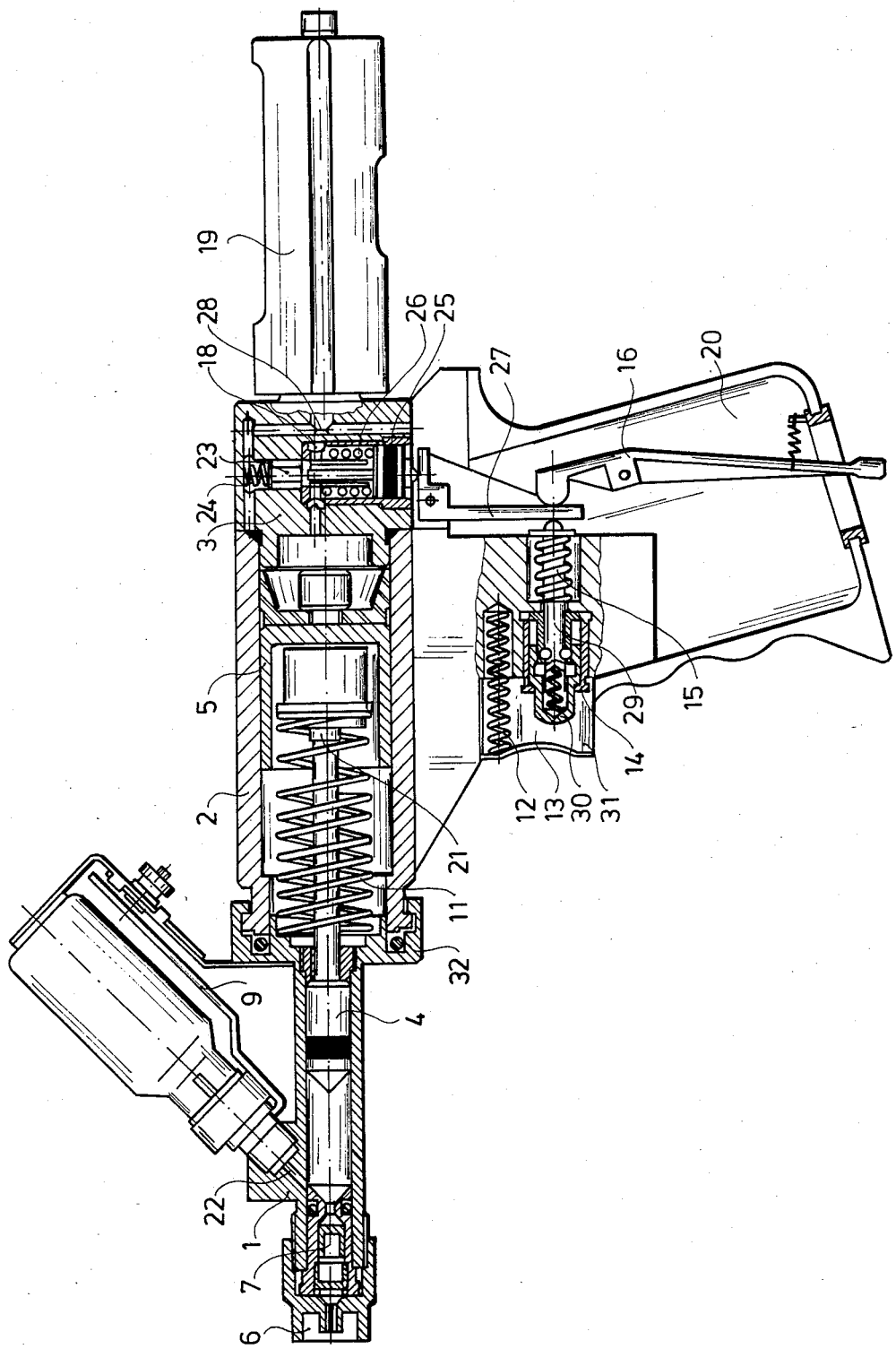

SIPHON-CARTRIDGE ACTIVATED AUTOMATIC INOCULATING DEVICE WIHTOUT NEEDLE FOR INDIVIDUAL ACCULATION, E.G. FOR INSULINIZATION

In course of the development of different technical means for therapeutical purposes inoculating devices without neddle have been developed which are able to introduce 1 to 1.5 cm³ vaccine into the organism by one-time injection, this quantity being sufficient in human therapeutics.

Out of these devices the Soviet product "Little bee", the USA-product "Jet", as well as the Hungarian patent "Viper" are worth to mention.

These devices receive the energy needed for shooting in a different way, by inserting an intermediate pressurizing unit.

Accordingly, pre-requisite of actuation used to be ensured by an oil-pump or a combined construction consisting of a lifting-hoisting lever and a lifting spindle.

General deficiencies of said inoculating devices lie in their complexity and complicated design, manipulation and maintenance require professional skill, dimensions and weight are considerable and productional costs are enermous.

Due to said deficiencies said inoculating devices could not be used in a wide circle, not even with people who are compelled to continuous insulinisation.

Primary aim of our invention is to eliminate said disadvantageous features, simultaneously to simplify structural design and to achieve a more modern form, at the same time to reduce considerably costs of production, to eliminate overdimensioning and to reduce weight, at last to simplify operation and maintenance.

Accordingly, the acculating device according to the invention represents a further developed form of the known inoculating device without needle, which is provided with an inoculating unit and and actuating unit connected thereto in a releasable manner, as well as a piston for the vaccine.

The essence of the improvement and invention, respectively, lies in that the inoculating device can be actuated by inserting a siphon-cartridge; in such a manner combined construction consisting of the lifting-hoisting lever and a lifting spindle—representing a rather complicated solution—having been used at the type "Viper" could be omitted.

As a result of the improved design the screw construction for the adjustment of the relative axial position of the shooting piston could be also omitted, which served—as a matter of fact—for adjusting the desired vaccine quantity but with a certain uncertainity, if the quantity of insuline had to be changed.

The construction indicating the vaccine quantity became also superfluous because, as in sense of the solution according to the invention vaccine quantity can be adjusted with the desired accuracy, as a consequence, problems connected to accidental displacement of the previously mentioned screw construction could be avoided.

The invention will be described by the aid of a preferred embodiment serving as an example, by means of the drawing enclosed showing the sectional side-view of the inoculating device according to the invention.

As it becomes obvious from the FIGURE, the inoculating device comprises an oculating unit and an actuating unit, these are interconnected with a coupling which can be quickly released by hand.

In the inoculating cylinder 1 which is joined to the front of the housing 2 by a quick coupling mechanism 32, there is the (shooting) inoculating piston 4 arranged, when it is displaced towards the actuating part, the vaccine flows from ampule 8 supported in yoke means 9, 10 into the inoculating cylinder 1. The back of the housing 2 contains a multifunction valve 18 placed into valve housing 3 and a gas cartridge placed in a support 19.

Moving of the inoculating piston 4 into said direction is performed by the returning spring 11.

On the end of the inoculating piston 4 facing the actuating part there is the ring 21 to be found, which is adjusting the required doses.

In course of the rear motion of the inoculating piston 4 the suction valve 22 provides for the introduction of the vaccine into the inoculating cylinder 1.

In case if the inoculating piston 4 is moving forward, the vaccine is leaving through the check-valve 7 and the inoculating head 6 which ensures inoculation without a needle.

The working piston 5 is arranged in the housing 2 and becomes actuated by the carbonic acid streaming through the pressure regulating valve 18 from the carbonic acid cartridge having been placed in a cartridge-support 19.

While moving, the bell crank lever 27 is lifting the piston 25, while the upper end thereof is putting into motion the sealing body 23 supported by the spring 24, in such a manner that the path to the working piston 5 through the channel-system formed in the actuating part is given free.

When the bell crank lever 27 is released, under the influence of the spring 28 the piston 25 gets into standstill, the carbonic acid performing the work is discharged through the bore 26 of the piston 25 into the atmosphere, while the sealing body 23 prevents further outstream of the carbonic acid from the cartridge.

When actuating the inoculating device by pulling the trigger 13 against the force of spring 12, the trigger pin 29 is moved against the starting spring 15 by means of the hoisting lever 16 as long as the three fixing balls 30 guided in sleeve-like housing 14 arrive at the bore of the trigger pin 29. The fixing balls 30 keep the trigger pin 29 in its frontal position.

After having pulled the trigger, it is moving the sliding sleeve as long as the fixing balls 30 are reaching the groove of the sliding sleeve 31. Now the released trigger pin 29 is moved backwards by the starting spring 15 and the bell crank lever 27 will be actuated.

What is claimed is:

1. Siphon-cartridge actuated automatic inoculating device without needle for individual inoculation, comprising an inoculating cylinder and an actuating unit, a quick coupling means (32) releasably interconnecting the inoculating cylinder (1) and the actuating unit (2), said actuating unit comprising a working piston (5), carbonic acid gas contained in a cartridge support for actuation of said unit is allowed to flow to a rear-side of the working piston (5) by a valve (18) performing a triple function and after actuation, said valve enabling a discharge of said gas into the atmosphere through a bore (26) of the piston, wherein after completing the phase of inoculation, further outstream of carbonic acid gas from the cartridge is prevented by a sealing body (23), wherein a spring (24) of the valve (18) performing triple function permits the discharge of the remaining carbonic acid gas from the cartridge for preventing a pressure drop, further comprising a starter spring connected to a trigger pin and a hoisting arm, said starter spring being placed into a state of readiness by said hoisting arm (16).

2. Inoculating device as claimed in claim 1, characterized in that adjustable reference means are provided for varying the vaccine quantity.

* * * * *